US009852277B2

United States Patent
Park et al.

(10) Patent No.: US 9,852,277 B2
(45) Date of Patent: Dec. 26, 2017

(54) METHOD FOR PERFORMING AUTHENTICATION USING BIOMETRICS INFORMATION AND PORTABLE ELECTRONIC DEVICE SUPPORTING THE SAME

(71) Applicant: Samsung Electronics Co., Ltd., Suwon-si, Gyeonggi-do (KR)

(72) Inventors: Gwang Ha Park, Seoul (KR); Do Hun Kim, Seoul (KR); Jin Ho Ahn, Yongin-si (KR); Dai-il Oh, Yongin-si (KR); Jae In Lee, Seongnam-si (KR); Hyun Suk Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 57 days.

(21) Appl. No.: 14/514,767

(22) Filed: Oct. 15, 2014

(65) Prior Publication Data

US 2015/0121514 A1 Apr. 30, 2015

(30) Foreign Application Priority Data

Oct. 31, 2013 (KR) .................. 10-2013-0130981

(51) Int. Cl.
*G06F 21/32* (2013.01)
*A61B 5/117* (2016.01)
(Continued)

(52) U.S. Cl.
CPC ............ *G06F 21/32* (2013.01); *A61B 5/1172* (2013.01); *A61B 5/1176* (2013.01); *G06F 21/34* (2013.01);
(Continued)

(58) Field of Classification Search
CPC ....... G06F 21/34; G06F 21/32; A61B 5/1176; A61B 5/1172; H04W 12/06; H04W 88/02;
(Continued)

(56) References Cited

U.S. PATENT DOCUMENTS 8,519,906 B2 * 8/2013 Richards ............... H01Q 19/30
343/718
9,646,300 B1 * 5/2017 Zhou .................... G06Q 20/206
(Continued)

FOREIGN PATENT DOCUMENTS

EP 1 545 102 A1 6/2005
JP 2009-525070 A 7/2009
(Continued)

OTHER PUBLICATIONS

Optimization and integration of electronic identity authentication using a biometric indicator and RFID, Peyravi et al, 10.1109/ICCIS.2010.5518565, IEEE, 2010.*

(Continued)

*Primary Examiner* — Jahangir Kabir
(74) *Attorney, Agent, or Firm* — Jefferson IP Law, LLP

(57) ABSTRACT

A method for performing authentication in a portable electronic device is provided. The method includes identifying whether a peripheral electronic device is located within a certain distance from the portable electronic device, receiving biometrics information from the peripheral electronic device when the peripheral electronic device is located within the certain distance from the portable electronic device, identifying whether the biometrics information received from the peripheral electronic device is identical to biometrics information stored in the portable electronic device, and releasing security set to the portable electronic device when the biometrics information received from the peripheral electronic device is identical to the biometrics information stored in the portable electronic device.

18 Claims, 7 Drawing Sheets

(51) Int. Cl.
*A61B 5/1171* (2016.01)
*A61B 5/1172* (2016.01)
*G06F 21/34* (2013.01)
*H04W 12/06* (2009.01)
*H04L 29/06* (2006.01)
*H04W 88/02* (2009.01)

(52) U.S. Cl.
CPC ..... *H04W 12/06* (2013.01); *G06F 2221/2111* (2013.01); *H04L 63/0853* (2013.01); *H04L 63/0861* (2013.01); *H04L 63/107* (2013.01); *H04W 88/02* (2013.01)

(58) Field of Classification Search
CPC ............. H04L 63/0853; H04L 63/0861; H04L 63/107
USPC ..................................... 726/1, 17, 19, 27, 29
See application file for complete search history.

(56) References Cited

U.S. PATENT DOCUMENTS

| | | |
|---|---|---|
| 2005/0136851 A1 | 6/2005 | Yamashita et al. |
| 2006/0210126 A1 | 9/2006 | Cho |
| 2007/0177770 A1* | 8/2007 | Derchak ............ G06K 9/00496 382/115 |
| 2009/0083850 A1 | 3/2009 | Fadell et al. |
| 2010/0225607 A1* | 9/2010 | Kim ........................ G06F 3/042 345/173 |
| 2011/0035338 A1* | 2/2011 | Kagan .................... G01D 4/002 705/412 |
| 2012/0009896 A1* | 1/2012 | Bandyopadhyay ... G06F 1/1643 455/411 |
| 2013/0061281 A1 | 3/2013 | Pao et al. |
| 2013/0129162 A1* | 5/2013 | Cheng .................... G06F 3/0304 382/124 |
| 2013/0201000 A1* | 8/2013 | Solomon .................. G05B 1/01 340/5.83 |
| 2013/0283351 A1* | 10/2013 | Palin .................. G06F 21/6218 726/4 |
| 2014/0282967 A1* | 9/2014 | Maguire ............... H04W 36/18 726/7 |

FOREIGN PATENT DOCUMENTS

| | | |
|---|---|---|
| JP | 2013-187879 A | 9/2013 |
| WO | 98-12670 A1 | 3/1998 |
| WO | 2014/089576 A1 | 6/2014 |

OTHER PUBLICATIONS

A biometric security based electronic gadget control using hand gestures, Garg et al, 10.1109/ICUMT.2009.5345495, IEEE, 2009.*

* cited by examiner

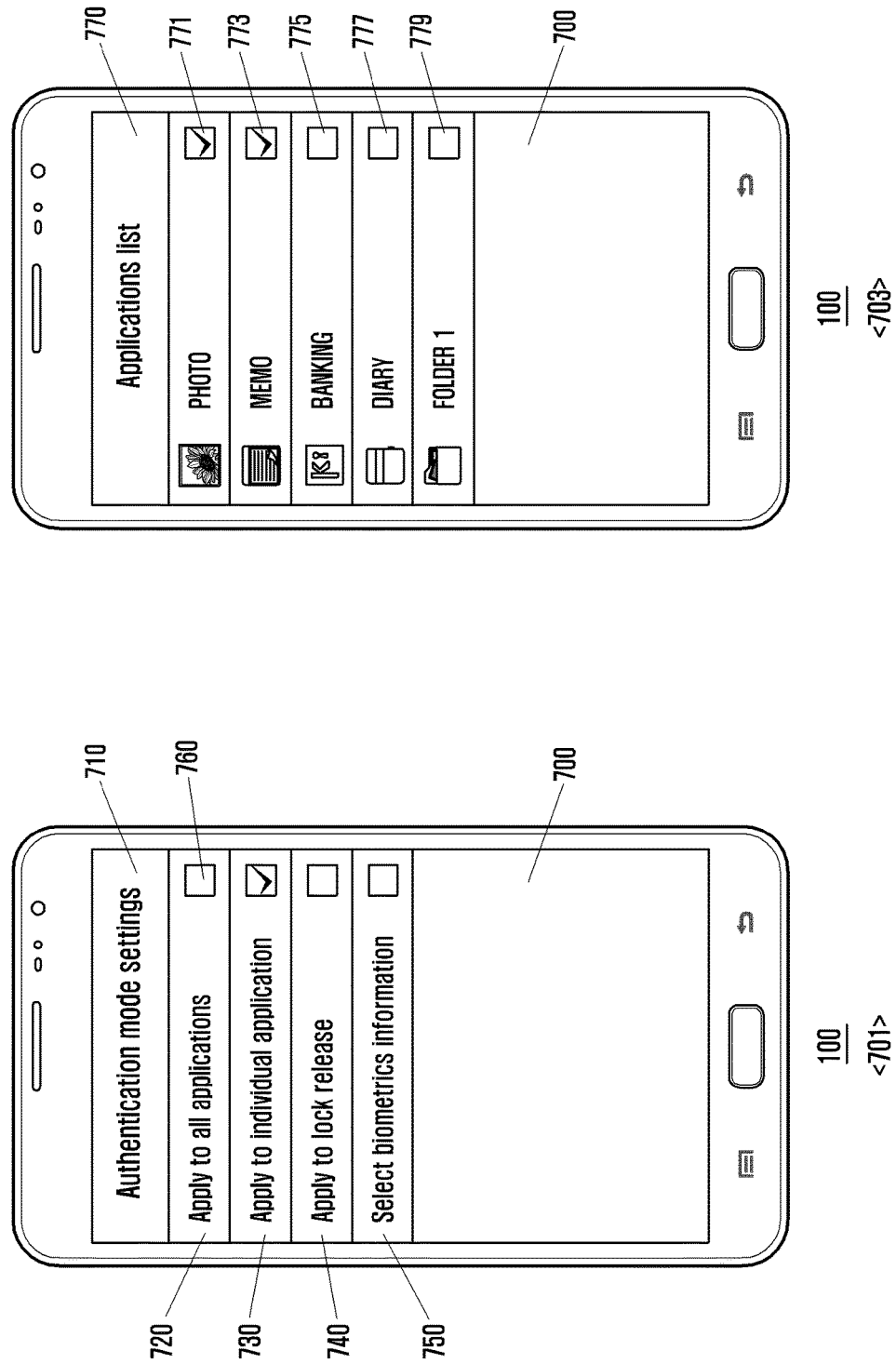

METHOD FOR PERFORMING AUTHENTICATION USING BIOMETRICS INFORMATION AND PORTABLE ELECTRONIC DEVICE SUPPORTING THE SAME

CROSS-REFERENCE TO RELATED APPLICATION(S)

This application claims the benefit under 35 U.S.C. §119(a) of a Korean patent application filed on Oct. 31, 2013 in the Korean Intellectual Property Office and assigned Serial number 10-2013-0130981, the entire disclosure of which is hereby incorporated by reference.

TECHNICAL FIELD

The present disclosure relates to a method for performing authentication using biometrics information and a portable electronic device supporting the same.

BACKGROUND

The supply and use of portable electronic devices are rapidly increasing according to dramatic developments in information and telecommunication technology, and semiconductor technology. Recently, portable electronic devices have been developing into mobile convergence devices which do not remain in their native area and expand to areas of other devices. Further, portable electronic devices have a more powerful computing capability and can use not only applications provided by a manufacturer of portable electronic devices, but also downloadable applications provided by various vendors. For example, various services, such as a mobile payment service, a mobile stock service, Internet banking, web browsing, a Social Network Service (SNS), games, a schedule management, a location-based service, and the like, became to be provided for the portable electronic device through applications.

Meanwhile, various services are being provided for the portable electronic device. However, there are issues, such as an inflow of malicious applications (for example, malignant code and spyware) and personal information leakage, and thereby the security of portable electronic devices must be reinforced. For example, various security methods, such as a Personal Identification Number (PIN), a password, or a log-in method are used to release a lock screen set to the portable electronic device, and a method of authenticating an individual user is used for applications and content (for example, photos, music, and documents) which require protection of personal information.

Recently, wearable electronic devices in ring, wristwatch, and glasses form which are worn on a human body became to take center stage. Accordingly, research and development are proceeding for performing various functions in portable electronic devices by combining with the wearable electronic devices.

However, the aforementioned security methods for portable electronic devices have inconveniences because authentication must be repeatedly performed every time a function is to be executed.

Therefore, a need exists for a method for performing authentication using biometrics information and a portable electronic device supporting the same.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method for performing authentication using biometrics information and a portable electronic device supporting the same in order to address the above mentioned inconveniences and to reinforce the security by combining with a wearable electronic device.

In accordance with an aspect of the present disclosure, a method for performing authentication in a portable electronic device is provided. The method includes identifying whether a peripheral electronic device is located within a certain distance from the portable electronic device, receiving biometrics information from the peripheral electronic device when the peripheral electronic device is located within the certain distance from the portable electronic device, identifying whether the biometrics information received from the peripheral electronic device is identical to the biometrics information stored in the portable electronic device, and releasing a security set to the portable electronic device when the biometrics information received from the peripheral electronic device is identical to the biometrics information stored in the portable electronic device.

In accordance with another aspect of the present disclosure, a portable electronic device for performing authentication using biometrics information is provided. The portable electronic device includes a short range communication module configured to receive a signal and biometrics information from a peripheral electronic device, and a control unit configured to identify whether a peripheral electronic device is located within a certain distance from the portable electronic device, to receive biometrics information from the peripheral electronic device when the peripheral electronic device is located within the certain distance from the portable electronic device, to identify whether the biometrics information received from the peripheral electronic device is identical to biometrics information stored in the portable electronic device, and to release security set to the portable electronic device when the biometrics information received from the peripheral electronic device is identical to the biometrics information stored in the portable electronic device.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 7 is a drawing illustrating a method of setting authentication by using biometrics information in a portable electronic device according to an embodiment of the present disclosure.

Throughout the drawings, it should be noted that like reference numbers are used to depict the same or similar elements, features, and structures.

DETAILED DESCRIPTION

Figure 1:
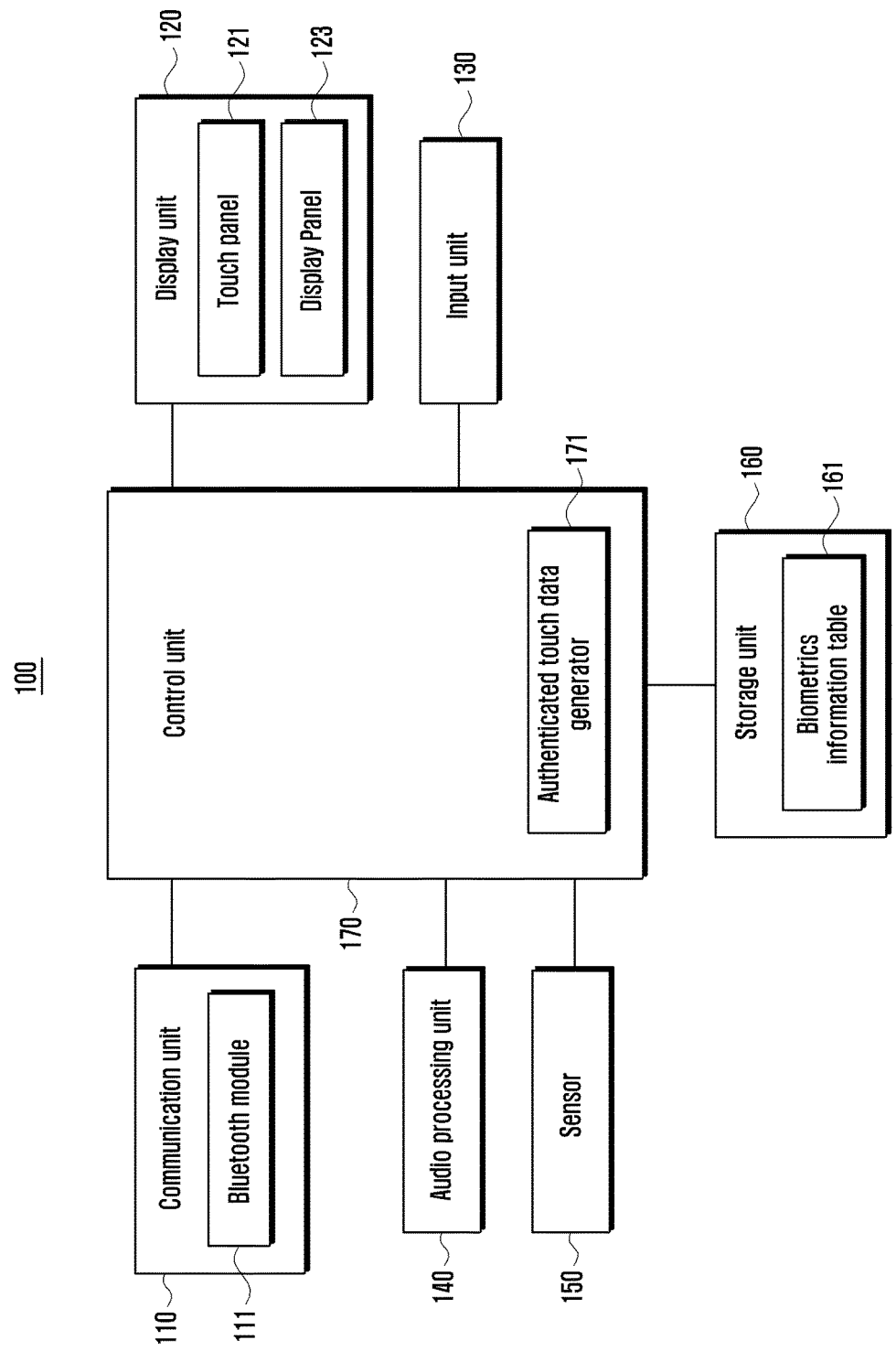
FIG. 1 is a block diagram illustrating a configuration of a portable electronic device according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

In various embodiments of the present disclosure, 'peripheral electronic device' refers to an electronic equipment which can transmit and receive data by connecting with a portable electronic device through a LAN (short range communication) module. Namely, the peripheral electronic device can be paired with the portable electronic device according to the various embodiments of the present disclosure through the LAN module, and may be a wearable electronic device which can be worn on a human body. Such a wearable electronic device may be provided in various forms, such as a ring, a wristwatch, glasses, a necklace, and the like. Further, the peripheral electronic device may include a sensor for collecting biometrics information. Here, the 'biometrics information' may include at least one of a user's fingerprint, a hand pattern, a face, a voice, an iris, a retina, and a vein.

Further, 'authentication touch data' is defined as data generated by combining user authentication information of biometrics information received from the peripheral electronic device and a touch event input by a user.

Further, 'authentication mode' is defined as a mode in which a user is authenticated by using biometrics information received from a peripheral electronic device and a certain function is performed accordingly.

Hereinafter, various embodiments of the present disclosure will be described based on a Bluetooth communication for convenience in description. However, the spirit and scope of the present disclosure is not limited to the Bluetooth system, and any other system supporting a LAN communication, such as a Wi-Fi Direct, can be applied to the various embodiments of the present disclosure.

The portable electronic device according to the various embodiments of the present disclosure may be configured in various forms. For example, the portable electronic device described in the present disclosure may include all the mobile communication terminals operating by communication protocols of various communication systems, such as a Portable Multimedia Player (PMP), a digital broadcast player, a Personal Digital Assistant (PDA), a music player (for example, a Motion Pictures Expert Group (MPEG-1 or MPEG-2) Audio Layer 3 (MP3) player), a portable game terminal, a smart phone, a notebook, a handheld Personal Computer (PC), a wearable PC, a wristwatch phone, and the like.

Hereinafter, various embodiments of the present disclosure are described with reference to the accompanying drawings. The same reference symbols are used throughout the drawings to refer to the same or like parts. Detailed descriptions of well-known functions and structures incorporated herein may be omitted to avoid obscuring the subject matter of the present disclosure.

For the same reasons, some components in the accompanying drawings are emphasized, omitted, or schematically illustrated, and the size of each component does not fully reflect the actual size. Therefore, the present disclosure is not limited to the relative sizes and distances illustrated in the accompanying drawings.

FIG. 1 is a block diagram illustrating a configuration of a portable electronic device according to an embodiment of the present disclosure.

Referring to FIG. 1, a portable electronic device 100 may include a communication unit 110, a display unit 120, an input unit 130, an audio processing unit 140, a sensor 150, a storage unit 160, and a control unit 170.

The communication unit 110 forms a certain communication channel with a supportable network (i.e., a mobile network) under the control of the control unit 170, and transmits and receives signals related to data communication services, such as a voice communication, a video communication, a Short Message Service (SMS), a Multimedia Messaging Service (MMS), the Internet, and the like. Further, the communication unit 110 may include a transmitter for amplifying and up-converting the frequency of a signal to be transmitted, and a receiver for low noise amplifying and down converting the frequency of a received signal. The communication unit 110 can perform data communication based on a message service by forming a communication channel for the message service under the control of the control unit 170. Here, the communication channel may include mobile communication channels, such as a Code Division Multiple Access (CDMA), a Time Division Multiple Access (TDMA), an Orthogonal Frequency-Division Multiple Access (OFDMA), and Internet communication channels, such as a wired Internet network and a wireless Internet network.

The communication unit 110 may include a Bluetooth module 111. The Bluetooth module 111 can perform transmission and reception of various data signals by forming a communication channel with a peripheral electronic device having a Bluetooth module under the control of the control unit 170. The Bluetooth module 111 can perform a Bluetooth communication with a peripheral Bluetooth device through a Bluetooth antenna by using a Bluetooth protocol. The Bluetooth module 111 can store a host stack for managing the Bluetooth communication, Bluetooth profile selected according to functions and conditions of an external Bluetooth device as communication objects, and application programs. The Bluetooth module 111 transmits a signal received from a peripheral electronic device to the control unit 170, if a paired peripheral electronic device approaches within a certain distance. The control unit 170 decides that the peripheral electronic device has approached within the certain distance from the portable electronic device 100, if the intensity of the received signal is greater than a critical value based on a Received Signal Strength Indicator (RSSI). If the peripheral electronic device approached the portable electronic device 100 within the certain distance, the control unit 170 controls the Bluetooth module 111 to receive user's biometrics information from the peripheral electronic device. Here, the biometrics information is at least one of a user's fingerprint, a hand pattern, a face, a voice, an iris, a retina, and a vein collected from the peripheral electronic device. However, the biometrics information is not limited to the above information and may include all the information which can identify a user by using the peripheral electronic device. The Bluetooth module 111 transmits the biometrics information received from the peripheral electronic device to the control unit 170. Further, the portable electronic device 100 can simplify a process of pairing with a peripheral electronic device through the Bluetooth module 111. Generally, in the process of connecting a Bluetooth communication, the Bluetooth module 111 receives a message for detecting a Bluetooth device according to a request from the peripheral electronic device (i.e., inquiry message), and transmits a signal including a remote address (BD ADDR) of the Bluetooth module 111 to the peripheral electronic device in response. The Bluetooth module 111 then performs a process of identifying a code received from the peripheral electronic device to authenticate the user of the peripheral electronic device. In the various embodiments of the present disclosure, the Bluetooth module 111 receives information including a code and biometrics information from the peripheral electronic device, and transmits them to the control unit 170. If the user is authenticated according to the biometrics information, the control unit 170 can control a Bluetooth connection (i.e., pairing) with the peripheral electronic device without a user interaction, such as a code confirmation. Similarly, the portable electronic device 100 automatically performs a process of identifying code for the authentication of the peripheral electronic device, and thereby the pairing between electronic devices can be done quickly without a user interaction.

The display unit 120 provides various screens required for operations of the portable electronic device 100. For example, the display unit 120 can support a waiting screen and a menu screen required for the operations of the portable electronic device 100. Such a display unit 120 may include a touch panel 121 and a display panel 123. The touch panel 121 may be configured with an add-on type of which the touch panel 121 is located on the display panel 123 or with an in-cell type of which the touch panel is inserted in the display panel 123.

The touch panel 121 generates a touch event responding to a user's gesture on a screen, and transmits the touch event to the control unit 170 by converting from an analog signal to a digital signal. The touch panel 121 may be a complex touch panel configured with a hand touch panel for detecting a hand gesture and a pen touch panel for detecting a pen touch. Here, the hand touch panel may be formed in a capacitive type, a resistive type, an infrared type, or an ultrasonic type.

The touch panel 121 may receive an input for setting an authentication mode. In the authentication mode, a user is authenticated by using biometrics information received from a peripheral electronic device, and a certain function is performed accordingly. The touch panel 121 may receive an input to decide whether to apply the authentication mode to all the applications or individual applications, whether to apply the authentication to a lock screen release of the portable electronic device 100, and to select biometrics information to be used for the authentication mode. If the authentication mode is applied to individual applications, the touch panel 121 may receive an input for selecting at least one application.

The display panel 123 displays data on a screen under the control of the control unit 170. Namely, if the control unit 170 processes data (for example, decoding) and stores in a buffer, the display panel 123 can display the data stored in the buffer on the screen by converting to an analog signal.

The display panel 123 may omit an output of security setting screen, if user authentication is performed by using biometrics information received from a peripheral electronic device under the control of the control unit 170. For example, the display panel 123 can directly display a waiting screen or a menu screen without outputting a certain screen for releasing a lock screen of the portable electronic device 100 (for example, without outputting a password input area), if a touch input is received when a lock screen and user authentication is performed under the control of the control unit 170. According to another embodiment of the present disclosure, the display panel 123 can directly output an application or contents execution screen under the control of the control unit 170 without outputting a certain screen to release the security of protected application or contents execution screen, such as a password input screen.

According to another embodiment of the present disclosure, the display panel 123 can output a screen set by a user under the control of the control unit 170. For example, the display panel 123 can release a lock screen of the portable electronic device 100 under the control of the control unit 170, and may output a certain object, such as an icon. Further, the display panel 123 can output an execution icon screen set by a user under the control of the control unit 170. For example, if the user touches a photo folder in an authentication mode, certain photos can be output.

According to another embodiment of the present disclosure, the display panel 123 can output a screen for setting an authentication mode. For example, the display panel 123 can output a screen under the control of the control unit 170 to decide whether to apply the authentication mode to all the applications or individual applications, whether to apply the authentication mode to a lock screen release of the portable electronic device 100, and to select biometrics information to be used for the authentication mode. Further, if the authentication mode is set to apply to individual applications, the display panel 123 outputs applications settable with security in a list, and may output a screen for selecting an application to be applied with the authentication mode from the output list.

The display panel 123 may be configured with a Liquid Crystal Display (LCD), Active Matrix Organic Light Emitted Diode (AMOLED), Passive Matrix Organic Light Emitted Diode (PMOLED), flexible display, or transparent display.

The input unit 130 transmits to the control unit 170 input signals of various characters and numerals, and input signals related to controls and settings of various functions in the portable electronic device 100. For this, the input unit 130 may include input keys and functions keys for inputting signals. The function keys may include direction keys, side keys, and shortcut keys for performing a specific function. Further, the input unit 130 may be configured with at least one of a touchpad, keypad of general key arrangement, QWERTY keypad, and their combination.

The audio processing unit 140 may include a codec, and the codec may be configured with a data codec for processing packet data and an audio codec for processing audio signals, such as a voice. The audio processing unit 140 outputs audio signals to a receiver RCV or a speaker SPK by converting a digital audio signal to an analog audio signal through the audio codec, and converts an analog audio signal received from a microphone to a digital audio signal through the audio codec. In the various embodiments of the present disclosure, the audio processing unit 140 can output a voice corresponding to a touch input function under the control of the control unit 170, if biometrics information received from a peripheral electronic device is identical to user's biometrics information pre-stored in the storage unit 160. For example, the audio processing unit 140 may output a voice, "Releasing lock screen," when a lock screen is set to the portable electronic device 100, if the biometrics information received from the peripheral electronic device is identical to the user's biometrics information pre-stored in the storage unit 160 and a user's touch is input through the display unit 120 of the portable electronic device 100.

The sensor 150 collects biometrics information. In the various embodiments of the present disclosure, the sensor 150 detects or measures user's biometrics information in real time to transmit to the control unit 170, if the biometrics information is received from the peripheral electronic device. For example, the sensor 150 can detect or measure corresponding to activated biometrics information under the control of the control unit 170, if at least one of a user's fingerprint, a hand pattern, a face, a voice, an iris, a retina, and a vein is received from the peripheral electronic device. The sensor 150 transmits the detected or measured biometrics information to the control unit 170, and the control unit 170 identifies whether the biometrics information received from the peripheral electronic device is identical to the biometrics information measured in real time.

Such a sensor 150 may include a fingerprint recognition sensor, a retina recognition sensor, an iris recognition sensor, a photoelectric sensor, such as a camera and infrared sensor, a pressure detecting sensor, and a motion sensor according to the type of biometrics information.

The storage unit 160 is an auxiliary memory unit (secondary memory unit) of the control unit 170, and may include a disk, Random Access Memory (RAM), and flash memory. The storage unit 160 stores data generated by the portable electronic device 100 under the control of the control unit 170, or data received from external devices, such as a server and a desktop PC through the communication unit 110 or an external interface (not shown). The storage unit 160 may include a biometrics information table 161.

The biometrics information table 161 can store at least one of biometrics information required for user authentication. In an embodiment of the present disclosure, the biometrics information table 161 can store a lock screen function, application, and contents function of the portable electronic device 100 in a list form to which the authentication mode is applied. In another embodiment of the present disclosure, the biometrics information table 161 can store functions to be authenticated according to the biometrics information in a certain table form. For example, the biometrics information table 161 may store settings so that user's fingerprint information is set to a lock screen release function and user's iris information is set to authentication of a protected application and contents. However, the present disclosure is not limited to the above examples. The biometrics information table 161 may store settings not only for individual biometrics information but also for individual functions of the portable electronic device 100.

Further, the storage unit 160 can store an Operating System (OS) for operations of the portable electronic device 100, programs required for optional functions, such as a sound play function, an image or video play function, a broadcasting play function, user data, and data transmitted or received while communicating. The storage unit 160 can store an authentication program using biometrics information. For example, the authentication program using biometrics information may include a routine for setting functions to be applied by the authentication mode, routine for deciding whether a peripheral electronic device approached the portable electronic device 100 within a certain distance, routine for analyzing biometrics information received from the peripheral electronic device, routine for comparing the analyzed biometrics information with pre-stored biometrics information or biometrics information measured (or detected) by the sensor 150, and routine for executing a function corresponding to a touch input if the analyzed biometrics information is identical to the biometrics information pre-stored or measured by the sensor 150. Further, the routine for executing a function corresponding to a touch input if the analyzed biometrics information is identical to biometrics information pre-stored or measured by the sensor 150 may include a subroutine which generates authentication touch data by combining the identical biometrics information and touch even information.

The control unit 170 controls general operations of the portable electronic device 100 and signal flows between internal components of the portable electronic device 100, and performs a function of processing data. The control unit 170 may include an authenticated touch data generator 171. The authenticated touch data generator 171 generates authentication touch data. For example, the control unit 170 receives biometrics information from a peripheral electronic device through the communication unit 110, and compares the received biometrics information with biometrics information pre-stored in the storage unit 160 or biometrics information detected by the sensor 150. According to the result of comparing, the control unit 170 decides to authenticate a user if the biometrics information received from the peripheral electronic device is identical to the pre-stored or detected biometrics information, and generates authentication touch data by combining the user authentication information and touch event information received from the touch panel 121. The authenticated touch data generator 171 may be included in the control unit 170 as shown in FIG. 1 or provided as a separate module.

The control unit 170 can control to release the security set to a function, such as a lock screen, and a protected application based on the authentication touch data. In the meantime, the control unit 170 can control a function according to touch event information included in the authentication touch data. For example, if a touch is input for selecting a photo folder set with security by a user, the control unit 170 releases the security set to the photo folder and controls the display unit 120 to output photos included in the photo folder. As another example, if the user inputs a touch in the portable electronic device 100 set with a lock screen, the control unit 170 can release the lock screen and control the display unit 120 to output a waiting screen or a menu screen. Further, the control unit 170 can control the display unit 120 to output a screen set by a user. For example, the control unit 170 can release a lock screen set to the portable electronic device 100 based on the authentication touch data and control the display unit 120 to output an object set by a user, such as an icon. Further, the control unit 170 can control the display unit 120 to output an execution screen set by a user based on the authentication touch data including touch event information for selecting an icon.

The configuration of portable electronic device 100 has been described for performing authentication using biometrics information according to an embodiment of the present disclosure, and hereafter a method for performing authentication using biometrics information is described according to another embodiment of the present disclosure.

Figure 2:
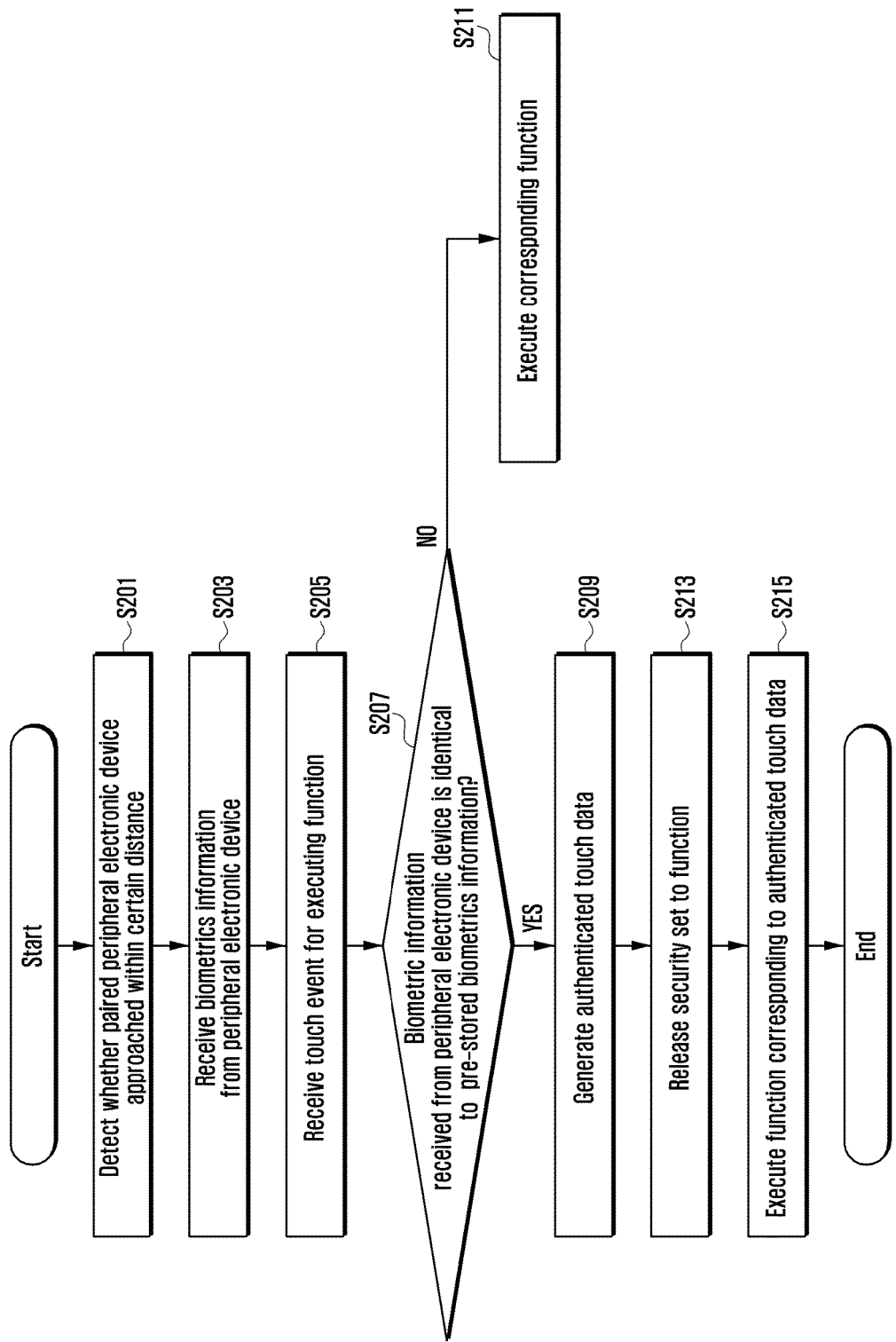
FIG. 2 is a flowchart illustrating a method for performing authentication by using biometrics information in a portable electronic device according to an embodiment of the present disclosure.

FIG. 2 is a flowchart illustrating a method for performing authentication by using biometrics information in a portable electronic device according to an embodiment of the present disclosure.

Referring to FIG. 2, the control unit 170 identifies whether a paired peripheral electronic device approached the portable electronic device 100 within a certain distance at operation 201. For example, the control unit 170 can receive a signal from a peripheral electronic device through the Bluetooth module 111. However, the Bluetooth module 111 is an example and the technical spirit of the present disclosure is not limited to the example. Namely, not only the Bluetooth module 111 but also any type of LAN supporting a connection between devices, such as a Wi-Fi Direct communication can be applied. The control unit 170 decides that the peripheral electronic device is located within the certain distance from the portable electronic device 100 based on the intensity of signal (RSSI) transmitted from the Bluetooth module 111.

If the paired peripheral electronic device is identified to be located within the certain distance at operation 201, the control unit 170 receives biometrics information from the peripheral electronic device through the Bluetooth module 111 at operation 203. Here, the biometrics information may be at least one of a user's fingerprint, a hand pattern, a face, a voice, an iris, a retina, and a vein collected by the peripheral electronic device. However, the biometrics information is not limited to the above information and may include all the information which can be collected by the peripheral electronic device and identify a user.

The control unit 170 receives a touch event from the touch panel 121 to execute a function at operation 205. For example, the control unit 170 can receive a touch event to release a lock screen set to the portable electronic device 100 and a touch event for executing an application.

The operations 203 and 205 may be performed at the same time. Namely, the peripheral electronic device can receive a touch input by a user after receiving biometrics information from the peripheral electronic device located in the certain distance or receive biometrics information from the peripheral electronic device at the same time when the user inputs a touch in the portable electronic device 100.

The control unit 170 identifies whether the biometrics information received from the peripheral electronic device is identical to pre-stored biometrics information at operation 207. For example, the control unit 170 can compare the received biometrics information with the biometrics information stored in the biometrics information table 161. The control unit 170 decides to authenticate a user if the received biometrics information is identical to the biometrics information stored in the biometrics information table 161.

If user authentication is decided at operation 207, the control unit 170 generates authentication touch data at operation 209. For example, the control unit 170 can generate the authentication touch data by using the user authentication information and touch event information received from the touch panel 121.

The control unit 170 controls to release security set to a function based on the authentication touch data at operation 213. For example, the control unit 170 can control to release security set to all the functions of the portable electronic device 100. For example, the control unit 170 can release security set for a lock screen of the portable electronic device 100 and protected applications set with a password based on the authentication touch data. Further, the control unit 170 can release security set for a portion of protected functions. For example, the control unit 170 analyzes touch event information included in the authentication touch data, identifies an application being executed by a touch, and releases the security if the application applied by an authentication mode is included in the biometrics information table 161.

The control unit 170 may omit a security release of protected functions based on the authentication touch data, or control so that an input for releasing the security is automatically performed. For example, if a lock screen is set to the portable electronic device 100, the control unit 170 can omit an input for releasing the lock screen, such as a password and a pattern based on the authentication touch data, or control so that a certain password or pattern is automatically input.

If the user authentication is not allowed at operation 207 in a case that a corresponding function, such as a lock screen is set to the portable electronic device 100, the control unit 170 controls to output a screen for releasing the lock screen at operation 211.

The control unit 170 controls to execute a function corresponding to the authentication touch data at operation 215. For example, the control unit 170 can control to execute a corresponding function by analyzing a touch event included in the authentication touch data. For example, if a user inputs a touch on a photo folder, the control unit 170 may control the display unit 120 to display photos included in the photo folder. As another example, the control unit 170 can perform a music contents if a user touches a music contents icon. Further, the control unit 170 can control the display unit 120 to output a screen set by a user. For example, the control unit 170 can release a lock screen set to the portable electronic device 100 based on the authentication touch data, and control the display unit 120 to output an object determined by the user, such as an icon. Accordingly, the control unit 170 can control the display unit 120 to output a screen determined by a user based on the authentication touch data including touch event information for selecting an icon.

Although not shown in FIG. 2, in an embodiment of the present disclosure, the control unit 170 can control to simplify a pairing process with a peripheral electronic device through the Bluetooth module 111. Generally in the process of connecting a Bluetooth communication, the Bluetooth module 111 receives a message for detecting a Bluetooth device (i.e., inquiry message) according to a request from a peripheral electronic device, and transmits a signal including a remote address (BD_ADDR) of the Bluetooth module 111 to the peripheral electronic device in response. The Bluetooth module 111 performs an operation of identifying a code received from the peripheral electronic device to authenticate a user. The control unit 170 receives information including a code and biometrics information from the peripheral electronic device through the Bluetooth module 111, and controls to connect a Bluetooth communication with the peripheral electronic device (i.e., pairing) by automatically identifying the code if the received biometrics information is identified to be identical to pre-stored biometrics information. If the biometrics information is received from the peripheral electronic device in the pairing process, the operation 203 for receiving biometrics information from the peripheral electronic device and the operation 207 for identifying whether the biometrics information received from the peripheral electronic device is identical to the pre-stored biometrics information may be omitted. Namely, if a touch event for executing a function is received at operation 205, the control unit 170 can skip to operation 209 and generate authentication touch data by combining the user authentication information and touch event information.

Figure 3:
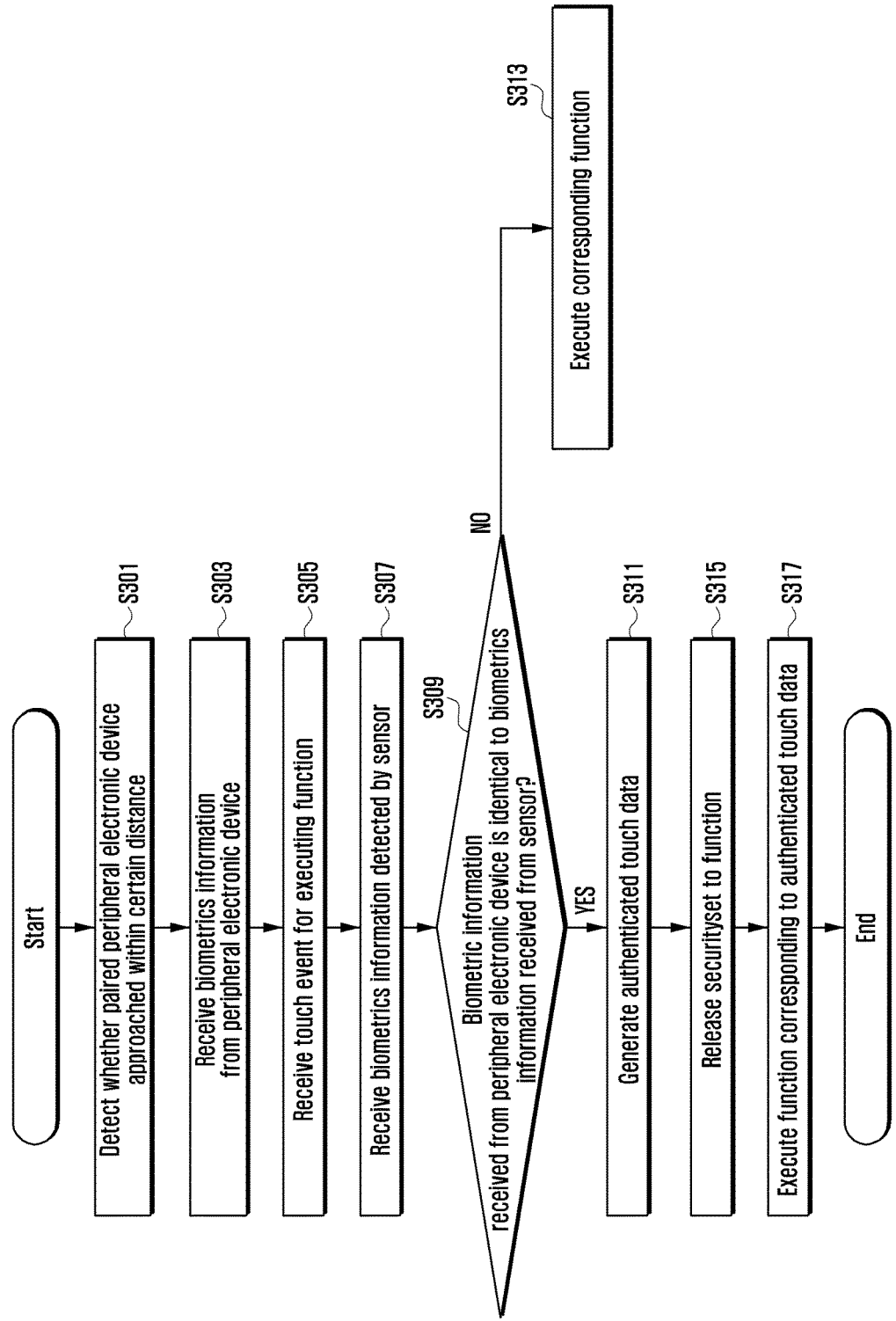
FIG. 3 is a flowchart illustrating a method for performing authentication by using biometrics information in a portable electronic device according to an embodiment of the present disclosure.

FIG. 3 is a flowchart illustrating a method for performing authentication by using biometrics information in a portable electronic device according to an embodiment of the present disclosure.

Referring to FIG. 3, the control unit 170 identifies whether a paired peripheral electronic device is located within a certain distance from the portable electronic device 100 at operation 301. If the paired peripheral electronic device is located within the certain distance at operation 301, the control unit 170 receives biometrics information from the peripheral electronic device through the Bluetooth module 111 at operation 303. The control unit 170 then receives a touch event for executing a function from the touch panel 121 at operation 305. As described above, the operations 301 to 305 may be identical to the operations 201 to 205 of FIG. 2.

If biometrics information is received from the peripheral electronic device at operation 303 or a touch event is received from the touch panel 121 at operation 305, the control unit 170 receives biometrics information from the sensor 150 by activating the sensor 150 at operation 307. For example, the control unit 170 decides whether to perform user authentication by comparing the biometrics information received from the peripheral electronic device with pre-stored biometrics information (for example, pre-registered user's fingerprint) as shown in FIG. 2. Alternatively, the control unit 170 can decide the user authentication by receiving biometrics information from the peripheral electronic device, activating the sensor 150, and comparing user's biometrics information detected through the activated sensor 150 with the biometrics information received from the at operation 307. For example, the user's biometrics information including at least one of a user's fingerprint, a hand pattern, a face, a voice, an iris, a retina, and a vein can be detected or measured by using an activated fingerprint recognition sensor, a retina recognition sensor, an iris recognition sensor, a photoelectric sensor, such as a camera and an infrared sensor, a pressure detecting sensor, and a motion sensor. Similarly, the control unit 170 can receive the biometrics information detected or measured by the sensor 150.

The control unit 170 identifies whether the biometrics information received from the peripheral electronic device is identical to the biometrics information detected or measured by the sensor 150 at operation 309. If the biometrics information received from the peripheral electronic device is identical to the biometrics information received from the sensor 150, the control unit 170 generates authentication touch data at operation 311. However, if the biometrics information received from the peripheral electronic device is not identical to the biometrics information received from the sensor 150, the control unit 170 controls to perform a function corresponding to a touch event at operation 313.

The control unit 170 controls to release security set for a protected function based on the authentication touch data at operation 315. Subsequently, the control unit 170 controls to perform a function corresponding to the authentication touch data at operation 317.

Figure 4:
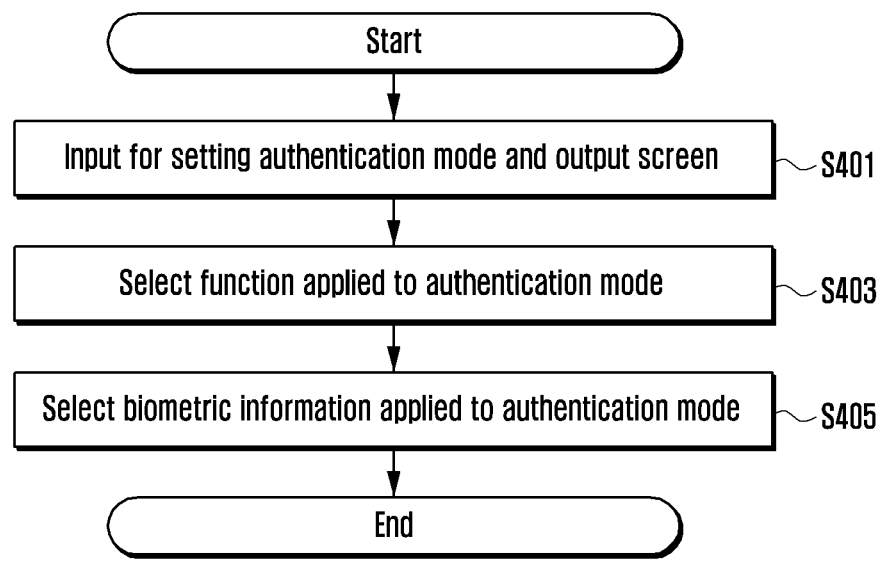
FIG. 4 is a flowchart illustrating a method for setting authentication by using biometrics information in a portable electronic device according to an embodiment of the present disclosure.

FIG. 4 is a flowchart illustrating a method for setting authentication by using biometrics information in a portable electronic device according to an embodiment of the present disclosure. However, the setting of the authentication using biometrics information may be omitted according to various embodiments of the present disclosure. For example, in the case that the portable electronic device 100 is designed by a designer so that all the securities set to the portable electronic device 100 are released if user authentication is performed by receiving at least one of biometrics information from a peripheral electronic device and confirming that the received biometrics information is identical to biometrics information stored in the portable electronic device 100, the setting of the authentication shown in FIG. 4 can be omitted.

Referring to FIG. 4, the control unit 170 receives an input for setting an authentication mode from a user and outputs a corresponding screen at operation 401. Here, the authentication mode refers to a mode in which a user is authenticated by using biometrics information received from a peripheral electronic device and a certain function is performed accordingly. For example, if the user selects a displayed icon for setting an authentication mode, the control unit 170 can output a screen in order to decide whether to apply the authentication to all the applications or a portion of applications, whether to apply the authentication to a lock screen of the portable electronic device 100, or to select at least one of biometrics information. However, such a screen output is an example, and various screens can be output for the authentication mod setting.

If the screen for setting an authentication mode is output at operation 401, the control unit 170 receives an input for selecting a function applied with the authentication mode, and sets the authentication mode to the function selected corresponding to the input at operation 403. For example, if the user selects to apply the authentication mode to all the applications, the control unit 170 may set so that the security can be released for all the protected applications, if the user is authenticated by confirming that biometrics information received from a peripheral electronic device is identical to biometrics information pre-stored or received from the sensor 150. Further, if the user selects to apply the authentication mode to individual applications, the control unit 170 controls the display unit 120 to output a screen for selecting an application to be applied by the authentication mode. For example, the control unit 170 can control the display unit 120 to output applications to be applied by the authentication mode in a list form. If the application to be applied by the authentication mode is selected by the user, the control unit 170 set the authentication mode accordingly.

The control unit 170 receives a user's input for selecting biometrics information to be applied to the authentication mode, and sets the authentication mode corresponding to the input for selection at operation 405. Specifically, a user's fingerprint, a hand pattern, a face, a voice, an iris, a retina, or a vein can be selected as biometrics information to be applied to the authentication mode. Further, the authentication mode can be set for at least one application according to the biometrics information as another embodiment of the present disclosure. For example, the control unit 170 may set so that a lock screen is released by user's fingerprint information and security set to an application or contents is released according to user's iris information.

Figure 5:
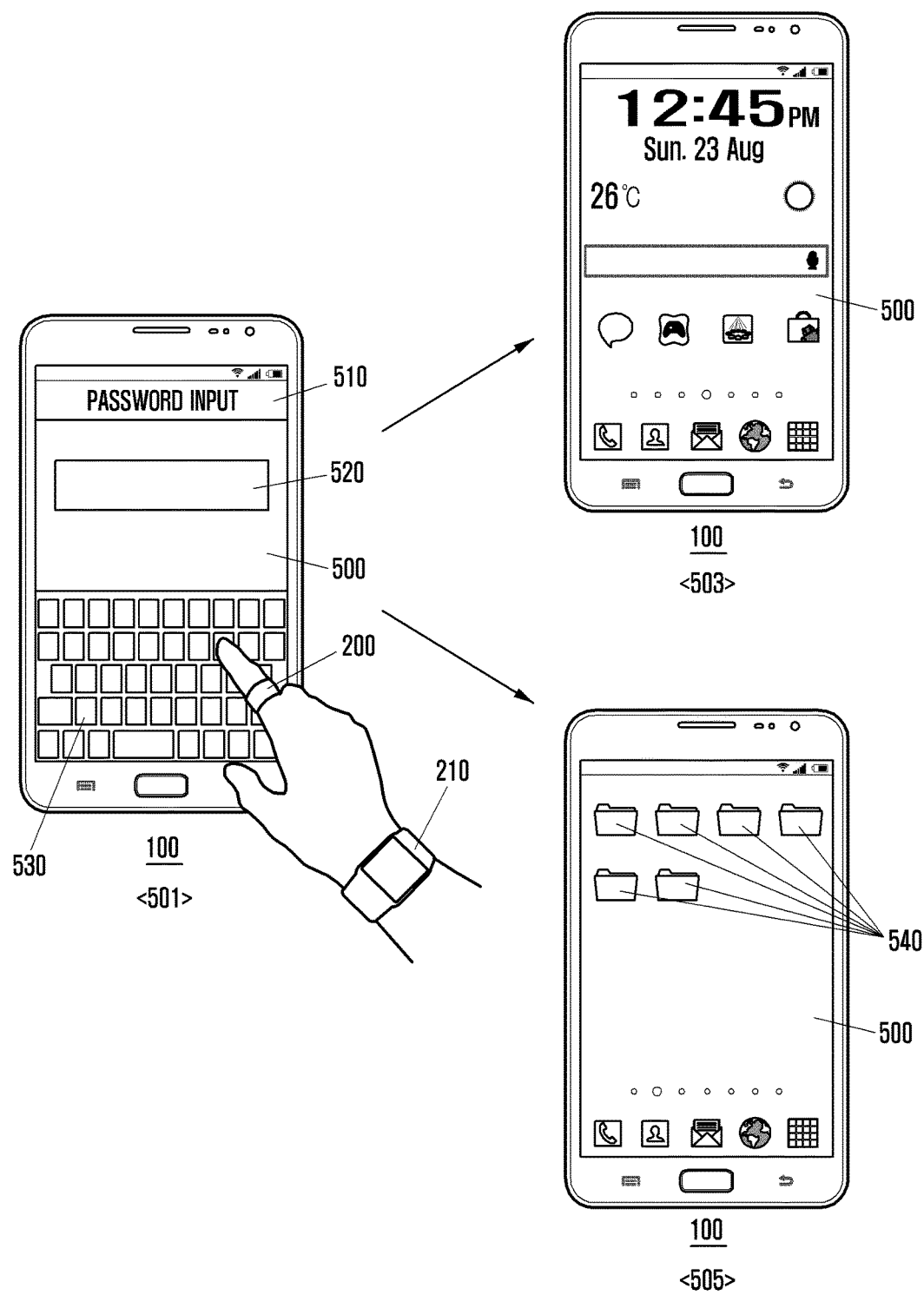
FIG. 5 is a drawing illustrating a screen output by releasing a lock screen in a portable electronic device according to an embodiment of the present disclosure.

FIG. 5 is a drawing illustrating a screen output by releasing a lock screen in a portable electronic device according to an embodiment of the present disclosure.

Referring to FIG. 5, reference number 501 illustrates a screen 500 displaying a state of lock screen set to the portable electronic device 100. The screen 500 includes a title 510 indicating a password input, a password input window 520, and keypad in a soft key form 530. If a peripheral electronic device 200 worn on a user's finger or a peripheral electronic device 210 worn on a user's wrist approaches within a certain distance from the portable electronic device 100, the control unit 170 of the portable electronic device 100 can receive biometrics information from at least one of the peripheral electronic devices 200 and 210. Here, the approach state of the peripheral electronic devices 200 and 210 may be decided by identifying whether the intensity of signal (Received Signal Strength Indicator (RSSI)) transmitted from a Bluetooth module of the peripheral electronic devices 200 and 210 to the Bluetooth module 111 of the portable electronic device 100 is greater than a critical value. Subsequently, the user may input a touch on the display unit 120. If a lock screen is set to the portable electronic device 100, an area of the screen 500 may be touched or a specific area may be touched to release the lock screen. If the user touches the screen 500, the control unit 170 compares the received biometrics information with biometrics information pre-stored in the portable electronic device 100, or with biometrics information detected or measured by the sensor 150, from which user authentication can be decided.

Reference number 503 shows an example of screen 500 for authenticating a user based on the received biometrics information. The password input window 520 disappears and a waiting screen 500 is displayed according to the release of lock screen. Reference number 505 shows a screen example determined by a user after setting an authentication mode and performing user authentication. For example, icons 540 determined by the user are displayed in the screen 500 of reference number 505.

Figure 6:
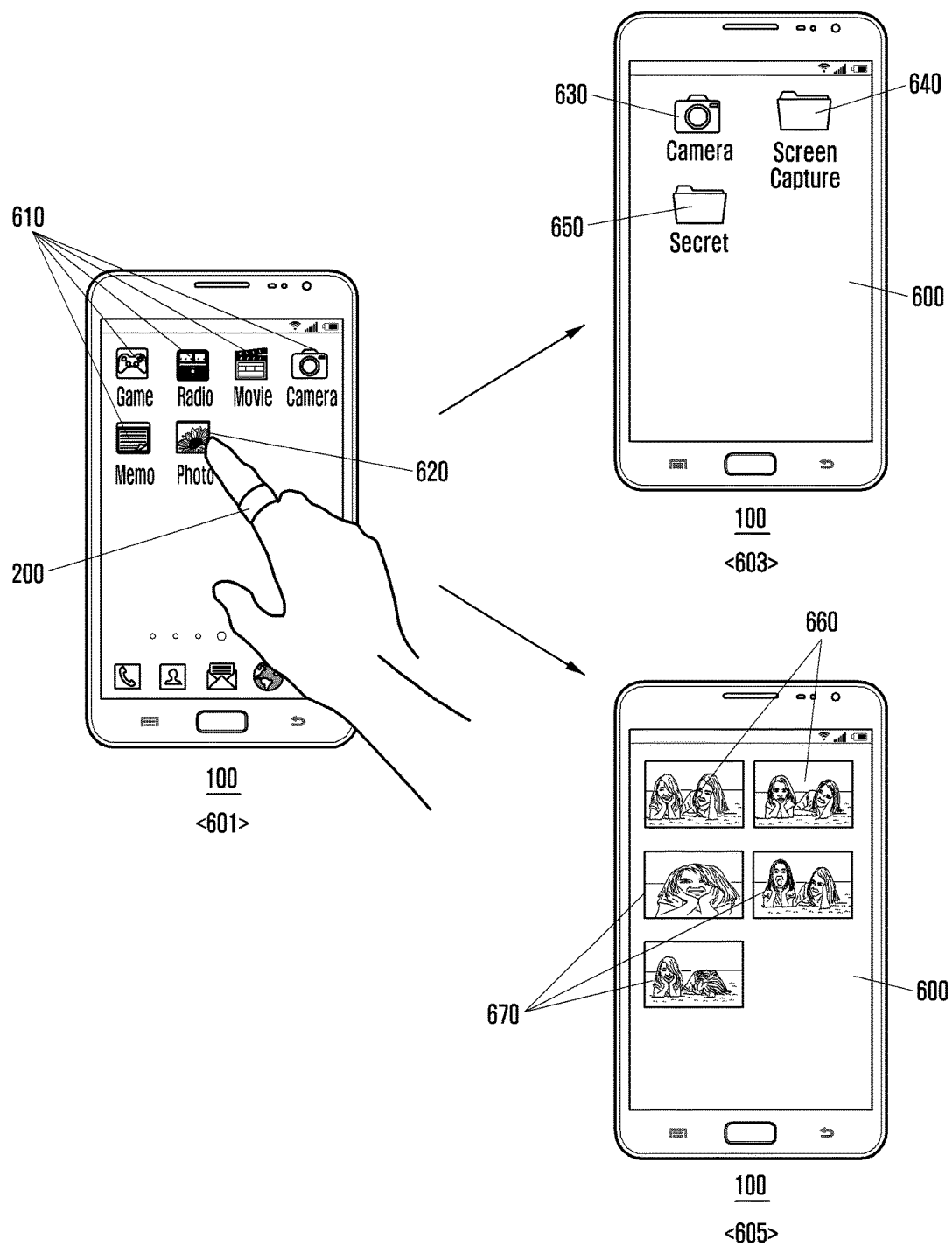
FIG. 6 is a drawing illustrating a screen output by executing an application in a portable electronic device according to an embodiment of the present disclosure.

FIG. 6 is a drawing illustrating a screen output by executing an application in a portable electronic device according to an embodiment of the present disclosure.

Referring to FIG. 6, reference number 601 shows a menu screen 600 outputting a protected photo folder 620 and a plurality of application icons 610. If a peripheral electronic device 200 worn on a user's finger approaches the portable electronic device 100 within a certain distance, the control unit 170 can receive biometrics information from the peripheral electronic device 200. If the user touches a photo folder icon 620 and the user is authenticated by using biometrics information received from the peripheral electronic device 200, icons 630, 640, and 650 included as subfolders of the photo folder are displayed without a separate authentication process as shown by reference number 603. If a "Secret" folder 650 is selected from reference number 603 by a user's touch, photos 670 determined by the user can be additionally output as shown by reference number 605. Namely, the portable electronic device 100 can be set to output photos 660 when the user authentication is not performed and to additionally output photos 670 determined by the user after the user authentication is performed. Similarly, if the user is authenticated by using biometrics information received from the peripheral electronic device 200, the security is automatically released and contents, such as additional photos 670 determined by a user can be output.

FIG. 7 is a drawing illustrating a method of setting authentication by using biometrics information in a portable electronic device according to an embodiment of the present disclosure.

Referring to FIG. 7, reference number 701 shows a screen 700 output for setting an authentication mode. The screen 700 can output a title 710 indicating an authentication mode setting, item 720 for selecting (760) whether to apply the authentication mode to all the applications, item 730 for selecting whether to apply the authentication mode to individual applications, item 740 for selecting a lock screen release of the portable electronic device 100, and item 750 for selecting at least one biometrics information to be applied to the authentication mode. However, such a screen output is an example and various screens can be output for setting the authentication mode.

Reference number 703 shows a screen 700 output when the authentication mode is applied to individual applications. The screen includes a title 770 indicating an application list, and items 771, 773, 775, 777, and 779 for selecting applications to be applied by the authentication mode. In the screen 700, a user can select a check box 771 and a check box 773 so that a photo folder function and a memo function are respectively applied by the authentication mode. The authentication is completely set if the user inputs a confirmation button after selecting the items.

In the meantime, the portable electronic device 100 can include various additional modules according to a designer's intention. Namely, the portable electronic device may further include components not described above, such as a LAN module, interface for transmitting and receiving data in a wired or wireless communication of the portable electronic device 100, an Internet module for performing an Internet network function, and a digital broadcasting module for receiving and playing a digital broadcasting. All the components cannot be listed here because the components variously change according to the trend of digital convergence. However, components having the same level as the above mentioned components can be further included in the portable electronic device 100. Further, it is clear to understand that the portable electronic device 100 according to the present disclosure can be configured by excluding or replacing specific components according to a designer's intention.

As described above, a method for performing authentication using biometrics information and a portable electronic device supporting the same according to various embodiments of the present disclosure provide a user with convenient authentication, security enhancement, and improved usability.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include Read-Only Memory (ROM), Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method for performing a user authentication in a portable electronic device, the method comprising:
   identifying a peripheral electronic device located within a certain distance from the portable electronic device;
   pairing the portable electronic device with the identified peripheral electronic device using a short-range communication protocol; and
   in response to the pairing of the portable electronic device:
   receiving the biometrics information and a code for connecting a communication with the peripheral electronic device from the peripheral electronic device;
   identifying whether the received biometrics information is identical to the biometrics information stored in the portable electronic device;
   confirming the code when the received biometrics information is identical to the biometrics information stored in the portable electronic device;
   releasing a security set to the portable electronic device in response to the identification that the biometrics information received from the identified peripheral electronic device is identical to the biometrics information stored in the portable electronic device and the successful verification of the code; and
   allowing access to the portable device based on the security set.

2. The method of claim 1, wherein the identifying of the peripheral electronic device located within the certain distance from the portable electronic device comprises:
   identifying whether a received signal strength indicator (RSSI) received by the portable electronic device is greater than a critical value.

3. The method of claim 1, wherein the biometrics information comprises at least one of a user's fingerprint, a hand pattern, a face, a voice, an iris, a retina, or a vein.

4. The method of claim 1, further comprising:
   receiving a touch event for executing a function of the portable electronic device; and
   generating an authentication touch data by combining the touch event information and user authentication information in order to identify whether the biometrics information received from the identified peripheral electronic device is identical to the biometrics information stored in the portable electronic device.

5. The method of claim 4, further comprising:
   executing a function corresponding to the generated authentication touch data,
   wherein the executing of the function corresponding to the generated authentication touch data includes at least one of outputting a certain object or outputting a certain content.

6. The method of claim 1, wherein the releasing of the security set to the portable electronic device comprises:
   releasing a lock screen set to the portable electronic device.

7. The method of claim 1, wherein the releasing of the security set to the portable electronic device comprises at least one of:
   releasing a security set for all protected applications in the portable electronic device; or
   releasing a security set for a portion of protected applications in the portable electronic device.

8. The method of claim 1, wherein the releasing of the security set to the portable electronic device releases at least one of a certain lock screen or a protected application according to at least one of biometrics information when the at least one biometrics information is received.

9. The method of claim 1, wherein the identifying of whether the biometrics information received from the peripheral electronic device is identical to the biometrics information stored in the portable electronic device comprises:
   activating a sensor of the portable electronic device when the biometrics information is received from the peripheral electronic device;
   detecting user's biometrics information through the activated sensor; and
   storing the detected user's biometrics information in the portable electronic device.

10. A portable electronic device comprising:
    a memory;
    a short-range communication processor coupled to the memory and configured to receive a signal and biometrics information from a peripheral electronic device; and
    a control processor coupled to the memory and configured to:

identify a peripheral electronic device located within a certain distance from the portable electronic device, pair the portable electronic device with the peripheral electronic device using a short-range communication protocol, and in response to the pairing of the portable electronic device, the control processor is further configured to:

receive the biometrics information and a code for connecting a communication with the peripheral electronic device from the peripheral electronic device, identify whether the received biometrics information is identical to the biometrics information stored in the portable electronic device, confirm the code when the received biometrics information is identical to the biometrics information stored in the portable electronic device, release a security set to the portable electronic device in response to the identification that the biometrics information received from the identified peripheral electronic device is identical to the biometrics information stored in the portable electronic device and the successful verification of the code, and allow access to the portable device based on the security set.

11. The portable electronic device of claim 10, wherein the control processor is further configured to identify whether a received signal strength indicator (RSSI) received by the portable electronic device is greater than a critical value.

12. The portable electronic device of claim 10, wherein the biometrics information comprises at least one of a user's fingerprint, a hand pattern, a face, a voice, an iris, a retina, or a vein.

13. The portable electronic device of claim 10, further comprising:

a touch panel configured to transmit a touch event for executing a function of the portable electronic device, wherein the control processor is further configured to generate an authentication touch data by combining the touch event information and a user authentication information in order to identify whether the biometrics information received from the identified peripheral electronic device is identical to the biometrics information stored in the portable electronic device.

14. The portable electronic device of claim 13, further comprising:

a display panel configured to output at least one of a certain object or a certain content;

wherein the control processor is further configured to:

execute a function corresponding to the generated authentication touch data, and control the display panel to output at least one of the certain object or certain content in order to execute the function corresponding to the generated authentication touch data.

15. The portable electronic device of claim 10, wherein the control processor is further configured to release a lock screen set to the portable electronic device in order to release the security.

16. The portable electronic device of claim 10, wherein the control processor is further configured to:

release at least one of the security set for the protected applications in the portable electronic device, and release the security set for a portion of protected applications in the portable electronic device with the security.

17. The portable electronic device of claim 10, wherein the control processor is further configured to release at least one of a certain lock screen or a protected application according to at least one of biometrics information when the at least one biometrics information is received.

18. The portable electronic device of claim 10, further comprising:

a sensor configured to detect user's biometrics information in order to identify whether the biometrics information received from the peripheral electronic device is identical to the biometrics information stored in the portable electronic device;

wherein the control processor is further configured to:

activate the sensor when the biometrics information is received from the peripheral electronic device, detect the user's biometrics information through the activated sensor, and store the detected user's biometrics information in the portable electronic device.

* * * * *